(12) United States Patent  
King

(10) Patent No.: US 7,909,527 B2  
(45) Date of Patent: Mar. 22, 2011

(54) FLUID DISPENSER

(75) Inventor: Timothy Paul King, Weybridge (GB)

(73) Assignee: Glaxo Group Limited, Middlesex (GB)

( * ) Notice: Subject to any disclaimer, the term of this patent is extended or adjusted under 35 U.S.C. 154(b) by 1107 days.

(21) Appl. No.: 11/568,864

(22) PCT Filed: May 12, 2005

(86) PCT No.: PCT/EP2005/005260
§ 371 (c)(1),
(2), (4) Date: Nov. 9, 2006

(87) PCT Pub. No.: WO2005/113155
PCT Pub. Date: Dec. 1, 2005

(65) Prior Publication Data
US 2007/0189839 A1    Aug. 16, 2007

(30) Foreign Application Priority Data
May 14, 2004    (GB) .................................. 0410839.5

(51) Int. Cl.
*A46B 11/00*    (2006.01)

(52) U.S. Cl. ....... 401/48; 401/188 R; 401/263; 401/265; 222/372

(58) Field of Classification Search .............. 401/188 R, 401/261–266, 48; 222/372, 378, 383.1, 566
See application file for complete search history.

(56) References Cited

U.S. PATENT DOCUMENTS 4,778,299 A *  10/1988  Coulter .......................... 401/48
6,406,207 B1 *  6/2002  Wiegner et al. ............... 401/272
6,422,777 B1    7/2002  Landrau et al.

FOREIGN PATENT DOCUMENTS

DE         10125666 A1   9/2002
WO      WO2004/024342 A   3/2004

* cited by examiner

*Primary Examiner* — David J Walczak
(74) *Attorney, Agent, or Firm* — Nora Stein-Fernandez; Theodore R. Furman

(57) ABSTRACT

A dispensing container for application of a fluid film forming substance to a surface, particularly a therapeutic film to a user's skin comprising a reservoir of a fluid film forming substance, a dispensing nozzle for the film forming substance, and a pump to send the substance from the reservoir through the dispensing nozzle. The dispensing nozzle comprises an elongate slot shaped aperture, and the dispensing container is adapted, particularly by a support extending from the side of the dispenser, so the nozzle can move adjacent to the surface in a direction transverse to the length direction of the slot whilst the substance is flowing through the aperture.

7 Claims, 3 Drawing Sheets

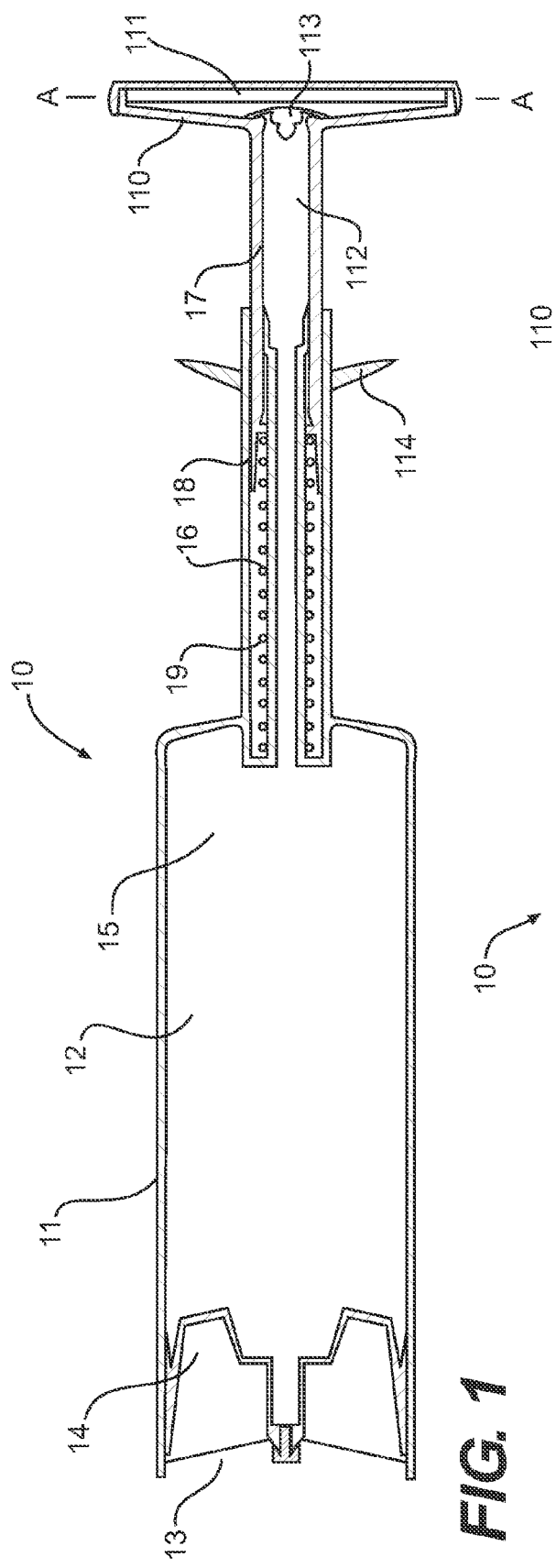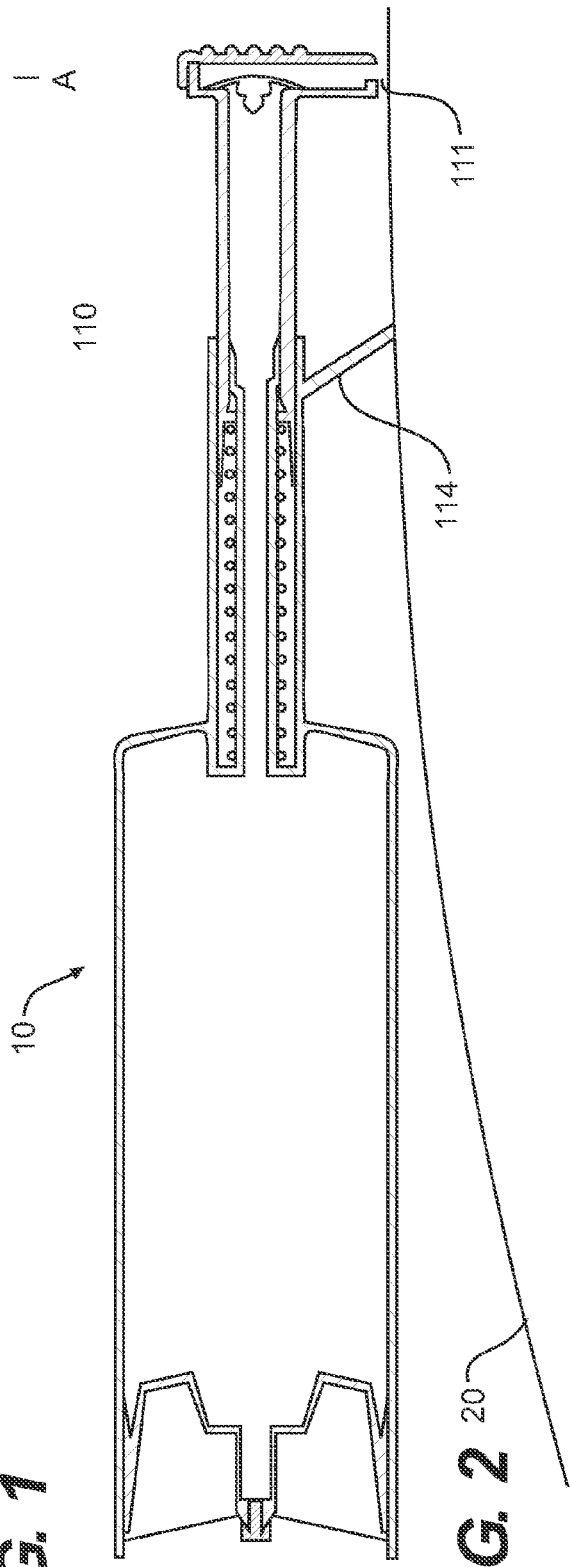

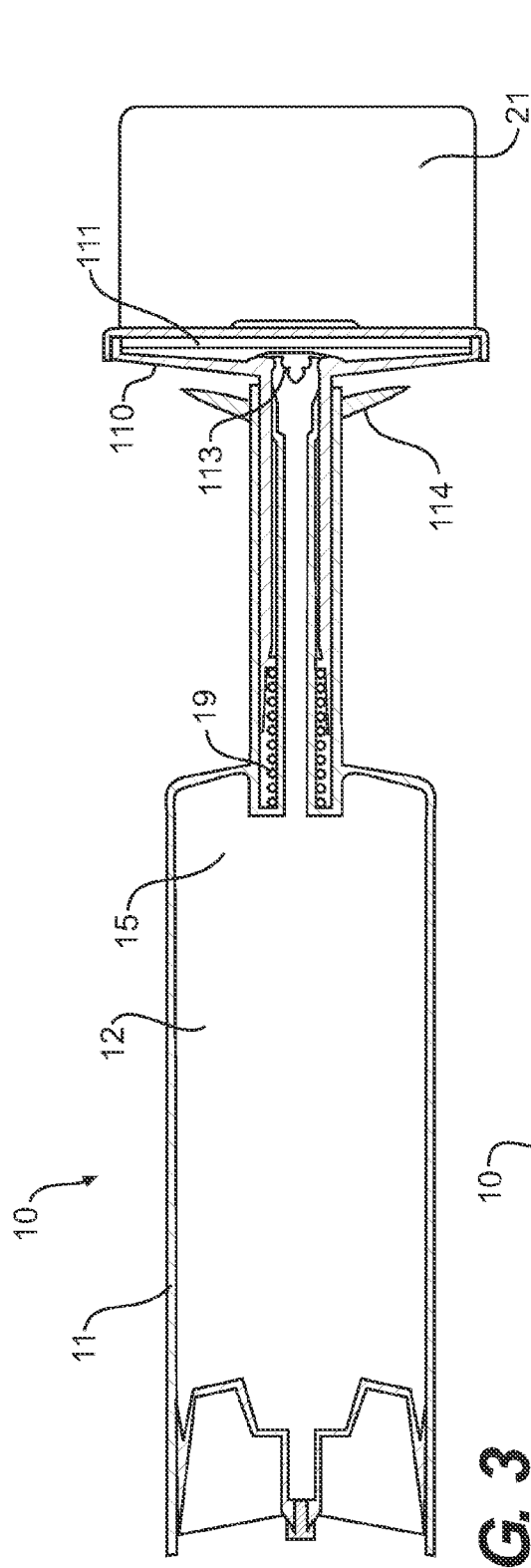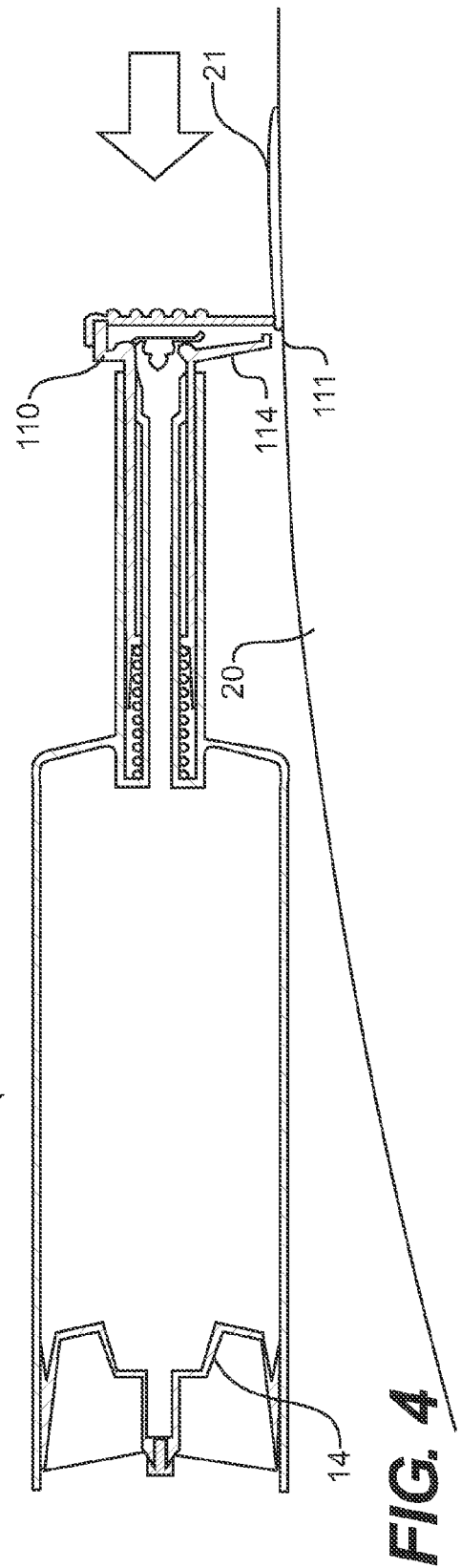

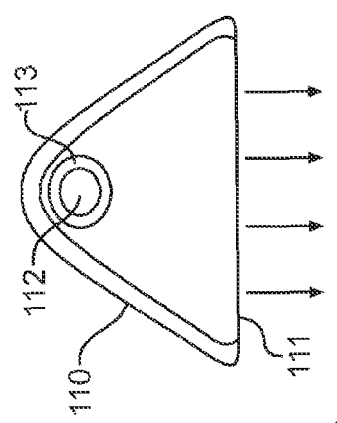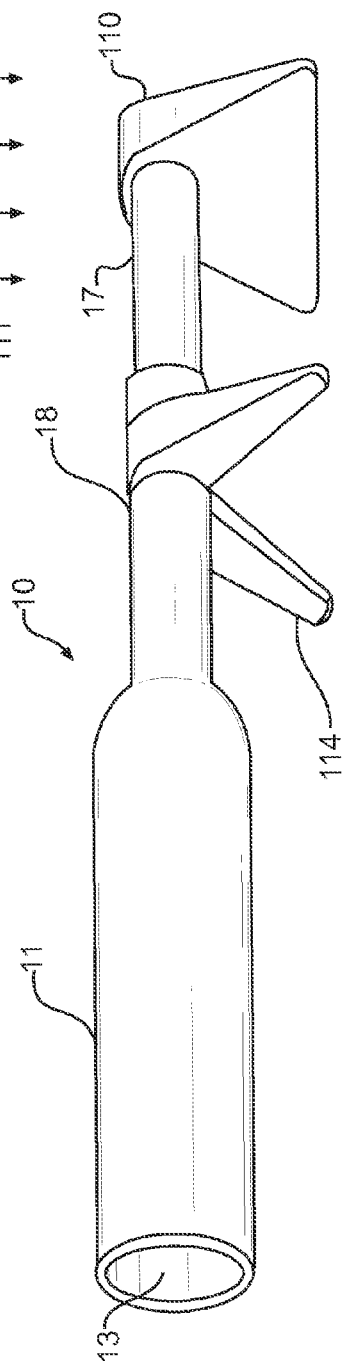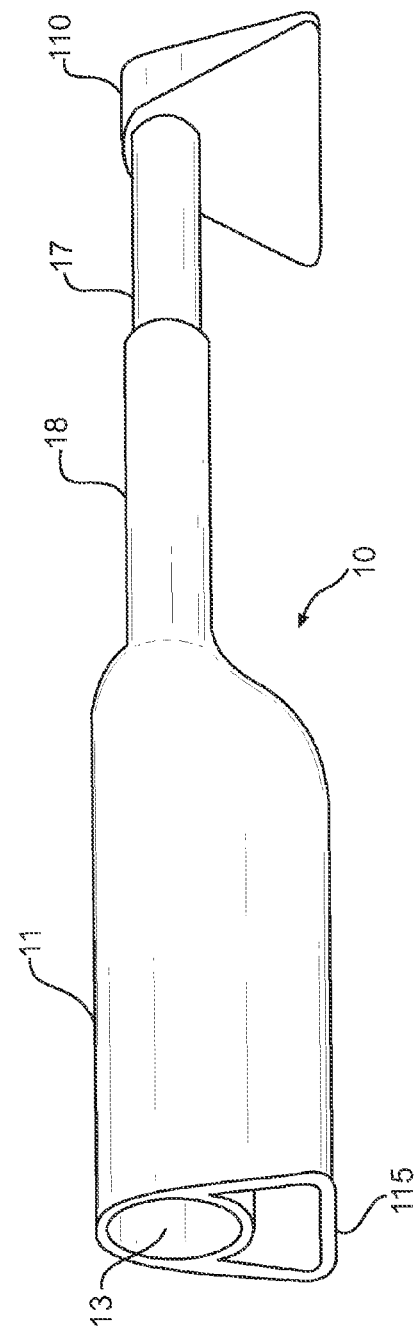

FLUID DISPENSER

This application is a §371 national phase entry of International Application No. PCT/EP2005/005260 filed May 12, 2005.

This invention relates to dispensing containers, in particular for dispensing a film-forming substance onto a user's skin.

In therapy films of materials are sometimes applied to a user's skin. For example a protective film may be applied to cover the site of a wound or another type of skin ailment. Medicament-containing films in the form of transdermal patches may also be also be applied to a user's skin to deliver the medicament through the user's skin. For example nicotine or nicotine analogues are delivered transdermally for smoking control therapy.

One way of applying a film to the user's skin is by applying a film-forming fluid substance to the skin and allowing the substance to develop into a solid or semi-solid, e.g. jelly-like, film. For example such a substance may comprise a solution or suspension of film forming ingredient(s) in a solvent which evaporates to form the film, or may comprise an ingredient which reacts with its environment to form a film. Such a substance may be applied to the skin by means of a suitable dispenser having a suitable dispensing nozzle.

Numerous dispensing containers for fluid materials are known, e.g. for cosmetic or therapeutic creams, soaps, adhesives, toothpastes etc. One type of such a dispensing container known e.g. for toothpastes and liquid soaps comprises a reservoir of the material communicating with a dispensing nozzle for the material, and a hand operable reciprocating pump to pump the material to the dispensing nozzle. A typical dispensing container of this type, now become well known, is shown in GB 804,095.

The problem still exists of providing an optimised dispensing container for applying a film-forming fluid substance to the skin. A particular problem is that of providing a cheap, simple, user-friendly, medically acceptable dispensing container which applies a film of optimum area and thickness, especially films of a consistent defined area and thickness. This is particularly important in situations where the film contains a medicament and the applied film needs to contain a defined dose of the medicament.

It is an object of this invention to address this problem. Other advantages of, and problems addressed by the invention will be apparent from the following description.

According to this invention a dispensing container for application of a fluid film forming substance to a surface is provided comprising;

a reservoir of a fluid film forming substance, a dispensing nozzle for the film forming substance, a means to send the substance from the reservoir through the dispensing nozzle, wherein the dispensing nozzle comprises an elongate slot shaped aperture, and the dispensing container is adapted to enable the nozzle to be moved adjacent to the surface in a direction transverse to the length direction of the slot whilst the substance is flowing through the aperture.

Typically the surface is a user's skin, the dispensing container being provided in a form suitable for use in applying a film to a user's skin.

The film forming substance may be a viscous liquid or fluid gel, which hardens after flowing through the aperture to form a solid or semi solid e.g. gel like film adherent to the user's skin. The substance may form a protective film on hardening and/or may include a medicament such as nicotine or a nicotine analogue for transdermal delivery from the film.

The reservoir may for example comprise a collapsible walled container which may be squeezed to extrude the substance therefrom via a conduit in fluid communication with the dispensing nozzle as a means to send the substance from the reservoir through the dispensing nozzle.

Preferably the reservoir comprises a container for the substance and the means to send the substance from the reservoir through the dispensing nozzle comprises a pump located between the container and the dispensing nozzle, the pump having an inlet communicating with the container and an outlet communicating with the nozzle.

The reservoir may be a replaceable reservoir, e.g. a reservoir which may be replaceably connected to the dispensing nozzle, so that when the contents of the reservoir are exhausted a new full reservoir may be connected to the nozzle. However the dispensing container provided by the invention can be of such simple and cheap construction that it is not economically worthwhile to have a replaceable reservoir, and the dispensing container may therefore be disposable when the reservoir is exhausted.

Suitably such a container may be a cylindrical container having the pump inlet at one cylindrical end and having an opposite open end, and with a so called floating piston of known type having a one way movement along the cylindrical container as the substance is progressively pumped from the reservoir to the dispensing nozzle. Preferably there is a one way valve, biased to allow flow of substance in the reservoir-toward-nozzle direction, between the reservoir and the nozzle. Such a one way valve may be between the reservoir and the pump, but is preferably between the pump and the nozzle. Such a valve can prevent suck-back of substance in the nozzle-toward-reservoir direction, and/or can prevent environmental contamination of the substance via the nozzle to the reservoir. Numerous types of one way valve are known and are suitable.

The pump is preferably a hand operable pump. A preferred type of pump is a reciprocating pump, i.e. a pump comprising reciprocally relatively moveable parts, such as a piston and cylinder or two reciprocally telescoping cylinders, which as they reciprocate successively increase the volume contained by them to suck a substance therein into the pump in an inlet stroke, then decrease the volume contained by them to pump a substance therein out of the pump in an outlet stroke. Numerous types of reciprocating pump are known.

The piston and cylinder, or the cylinders, are preferably biased toward the inlet stroke movement, providing the advantage that the user need only apply the outlet stroke, the bias providing the inlet stroke. Such bias may be provided for example by a biasing spring operating between the pump piston and pump cylinder, or operating between telescoping cylinders. Typically springs are made of metal and it is desirable to construct the pump in such a way that a metal spring does not come into contact with the substance, to avoid risk of interaction between the substance and the spring.

An advantage of a reciprocating pump is that the dispensing nozzle may be connected to e.g. made integrally with one of the reciprocating parts e.g. the cylinder or the piston, or one of the telescoping cylinders, and the reciprocal movement of the reciprocating part and nozzle during the outlet stroke can guide the nozzle in a linear direction along the surface to which the substance is to be applied, whilst the substance is flowing through the aperture during the outlet stroke. When the reservoir is an elongate, e.g. cylindrical, reservoir preferably the pump reciprocates along a direction parallel to the long, e.g. cylindrical, axis of the reservoir.

A particular arrangement of reservoir and reciprocating pump comprises a pump piston integral with the reservoir and having a pump inlet conduit passing through the piston and in communication with the reservoir, the pump piston being situated within a pump cylinder which is reciprocally slideably moveable relative to the piston and reservoir, and which is integral with and in communication with the dispensing nozzle, with a one way valve between the cylinder and the nozzle biased to allow flow of substance toward the nozzle.

To operate such a pump the cylinder and hence the nozzle are moved by the user in the outlet stroke slidingly over the piston against the bias, the substance exiting via the nozzle, until a suitable amount of the substance has been applied. Preferably the output stroke of the pump is limited by endstop abutment of the reciprocal pump parts at the limit of their relative movement. The bias can then move the cylinder in the opposite direction in the inlet stroke.

The amplitude of the relative reciprocal movement and hence the amount of substance delivered during the outlet stroke can be limited and consequently metered by for example end-stop abutments. For example the pump may be provided with variable end stops so that the amplitude may be set to vary the volume dispensed and/or the length the nozzle moves during the pump outlet stroke. If the outlet nozzle is integral with the reciprocally moving part this limitation of amplitude can also limit the distance the nozzle moves, to thereby limit and control the area of the so formed film. A suitable length of outlet stroke for application of a patch of medicament containing film-forming material is 3-4 cm.

The elongate slot shaped aperture of the dispensing nozzle facilitates the dispensing of the substance onto the user's skin in the form of a strip having a width substantially the same as the length of the aperture as the nozzle is moved in a direction transverse to the length direction of the slot whilst the substance is flowing through the aperture. The dimensions of the elongated slot can be determined experimentally based on for example the viscosity of the substance and the amount of substance it is desired to apply to a surface such as a user's skin. Typically the width of the slot across is elongate length direction may be 0.1-1 mm, and the length of the slot along its longitudinal direction may be 1-2 cm.

Suitably the nozzle is shaped and aligned to direct flow of the substance in a direction transverse to, preferably perpendicular to, the direction in which the nozzle is moved adjacent to the skin surface, and transverse to, preferably perpendicular to, the length direction of the slot shaped aperture. Suitably the slot shaped aperture comprises the outlet opening of a manifold into which the substance is sent from the reservoir, e.g. into which the substance is pumped by the pump via an inlet opening into the manifold, and at which the one way valve may be located. Preferably, to apply a film of uniform thickness to the skin the manifold is constructed so that a uniform flow of substance is achieved along the whole length of the slot shaped aperture. This may be achieved by the use of a so called "centre-fed coat hanger manifold" (term of the art). Internally such a manifold comprises a cavity which, as cut in a direction perpendicular to the direction in which the nozzle is moved adjacent to the skin surface, e.g. in a direction parallel to the length direction of the slot is of an overall generally triangular (which may have curved sides) section, preferably equilateral or isosceles, with the slot shaped aperture along a lower base edge of the cavity and the inlet opening into the manifold near the opposite upper apex of the triangle, e.g. in the upper half of the triangular shape. Such a manifold is preferably constructed in a known way as to reduce die swell effects from its centre fed point to deliver a film of uniform depth across the width of its slot-shaped opening. In the direction parallel to the direction in which the nozzle is moved adjacent to the skin surface, e.g. in a direction perpendicular to the length direction of the slot such a manifold is typically internally flattened, e.g. having a dimension in this direction in the range 0.05-0.2 of the length of the slot.

The dispensing container of the invention may be adapted to enable the nozzle to be moved adjacent to the skin surface in a direction transverse to the length direction of the slot in various ways.

In one preferred way the dispensing container is provided with a support by which the dispensing container may be held against the user's skin whilst the nozzle is moved during the outlet stroke. Such a support may help to space the nozzle at a suitable distance from the user's skin surface, may help to keep the dispensing container in a suitable position for use, and may help to guide the nozzle in its movement along the user's skin. For example in a dispensing container comprising the above-mentioned reservoir and reciprocating pump system, such a support may be of dimensions such that when the support is in contact with a surface such as a user's skin, the nozzle may be held in contact with the surface or immediately adjacent to the surface, and the direction along which the pump reciprocates is substantially parallel to the surface. In such a dispensing container, a constructed line between the parts of the support and nozzle which in use are closest to or in contact with the skin is substantially parallel to this direction along which the pump reciprocates. The support may for example comprise one or more projection from the outer surface of the dispensing container e.g. one or preferably two legs extending therefrom. For example the support(s) may extend in a direction transverse e.g. perpendicular to the direction in which the nozzle is to be moved adjacent to the surface. For example in a dispensing container incorporating a reciprocal pump the support(s) may extend in a direction transverse e.g. perpendicular to the reciprocating direction of the pump. Such a dispensing container may be held by a user adjacent to the skin surface with the support against the skin surface and with the nozzle adjacent to the skin surface, for example typically 1 mm or less from the skin surface, and the nozzle moved adjacent to and parallel to the skin surface in a direction transverse to the length direction of the slot to pump the substance through the aperture.

In another way the dispensing container, for example the container, may have an outer profile shaped and positioned relative to the nozzle such that when in use this outer profile is placed against a surface such as the user's skin, the nozzle is positioned at a suitable distance from, e.g. adjacent to or in contact with the surface. For example in a dispensing container comprising the above-mentioned reservoir and reciprocating pump system, the dispensing container may be such that when the profile is in contact with a surface such as a user's skin, the nozzle is positioned in contact with the surface or immediately adjacent to the surface, and the direction along which the pump reciprocates is substantially parallel to the surface. Such a profile may be substantially planar in a direction parallel to the direction along which the pump reciprocates, and the nozzle is preferably in the plane of this planar surface. Such a dispensing container may be held by a user adjacent to the skin surface with the outer profile against the skin surface and with the nozzle adjacent to the skin surface, for example typically 1 mm or less from the skin surface, and the nozzle moved adjacent to and parallel to the skin surface in a direction transverse to the length direction of the slot to pump the substance through the aperture.

Therefore a preferred construction of the dispensing container of this invention comprises an elongate container for the substance and a hand operable reciprocating pump which reciprocates along a direction parallel to the long axis of the container and is located between one end of the container and the dispensing nozzle, the pump having an inlet communicating with the container and an outlet communicating with the nozzle, the pump being biased toward the inlet stroke movement, with a one way valve between the pump and the nozzle biased toward flow of substance in the cylinder-toward-nozzle direction, the reservoir provided with a support by which the reservoir may be held against a user's skin whilst the nozzle is moved during the outlet stroke of the pump, the nozzle comprising a manifold into which the substance is pumped from the reservoir and having a slot shaped aperture shaped and aligned to direct flow of the substance in a direction perpendicular to the direction in which the nozzle is to be moved adjacent to the skin surface and transverse to the length direction of the slot shaped aperture.

The reservoir, piston, pump piston and manifold of the dispensing container of this invention may be made of conventional plastics materials such as polypropylene, and the valve may comprise an elastomeric material, as normally used for dispensing containers for medicament substances.

The invention also provides a method of applying a fluid film forming substance to a surface, typically a user's skin, using a dispensing container as described herein.

The invention will now be described by way of example only with reference to the accompanying drawings which show:

FIGS. 1 and 2 Longitudinal sections through a dispensing container of this invention prior to an outlet stroke.

FIGS. 3 and 4 Longitudinal sections through the dispensing container of FIG. 1 after an outlet stroke.

FIG. 5 sectional view through the nozzle of the dispensing container of FIGS. 1 to 4.

FIG. 6 Perspective view of the dispensing container of FIGS. 1 to 4.

FIG. 7 Perspective view of an alternative form of the dispensing container.

Parts listed in these drawings are:
10 dispensing container overall
11 reservoir
12 fluid film forming substance
13 open end
14 floating piston
15 pump inlet
16 piston
17 pump cylinder
18 outer cylinder
19 spring
110 manifold
111 dispensing nozzle
112 inlet opening into manifold
113 one way valve
114 support
20 skin surface
21 film Referring to FIGS. 1 to 4, a dispensing container 10 overall is shown in a sectional side view FIG. 1, and a sectional plan view FIG. 2. This comprises a reservoir 11 containing a fluid film forming substance 12. The reservoir comprises a cylindrical container for the substance 12 having an open end 13, and has a so called floating piston 14 of known type having a one way movement along the cylindrical container from left to right as shown. At the opposite end of the cylindrical container 11 is a pump inlet 15 and a piston 16 which is integral with the reservoir 11, the pump inlet 15 passing through a piston 16 coaxial with cylindrical reservoir 11 to provide communication with the reservoir 11.

The piston 16 comprises a part of a reciprocating pump comprising a pump cylinder 17 within which the piston 16 is situated and forms a sliding seal with the inner surface of the cylinder 17 at the end of the piston 16 remote from the reservoir 11, the cylinder 17 being slideably moveable relative to the piston 16 and reservoir 11. The cylinder 17 is further slideably located within an outer cylinder 18, and a spring 19 is located within this outer cylinder 18 to bias the cylinder toward a position distant from the cylinder 11.

The pump cylinder 17 is integral with and in communication with a manifold 110, which incorporates dispensing nozzle 111. Manifold 110 is constructed in two parts which snap-fit or are otherwise connected together. The nozzle 111 is in the form of an elongate slot shaped aperture facing in a direction perpendicular to the cylindrical axis of the container 11 and of the piston 16, i.e., as shown in FIG. 2, having a length direction perpendicular to the plane of the drawing. The slot shaped aperture comprises the outlet opening of the manifold 110 into which the substance is pumped from the reservoir 11 by the pump 16, 17 via an inlet opening 112 into the manifold 110, and there is a one way valve 113 between the pump 16, 17 and the manifold 110, biased to allow flow of substance toward the nozzle 111. The manifold 110 is a so called centre-fed coat hanger manifold (term of the art).

As seen in FIG. 5, which shows a section through the manifold 110 cut along the line A-A of FIG. 1, internally the manifold 110 comprises a cavity of an overall generally isosceles triangular section with the slot shaped aperture 111 along a lower (as seen) edge of the cavity and the inlet opening 112 of the manifold 110 with valve 113 near the upper (as seen) apex of the triangular shape. The cavity within manifold 110 is dimensioned to include as little internal space as possible to avoid accumulation of unused substance in manifold 110.

The container 11, piston 16, cylinder 17 and manifold 110 are made by injection moulding of PP 4018 polypropylene (BP Amoco), this being a suitable polypropylene.

To enable the dispensing container 10 to be properly positioned on the user's skin surface 20 the dispensing container is provided with a support 114 which comprises two legs extending from the outer cylinder 18 in a direction perpendicular to the longitudinal cylindrical axis.

The dispensing container operates as follows. The dispensing container is initially in the configuration shown in FIG. 1, with the reservoir 11, pump cylinder 17 and piston 16 full of the substance, and the cylinder 17 in the position shown in FIG. 1, i.e. more distanced from reservoir 11 along the cylindrical axis. The dispensing container is placed adjacent the user's skin surface 20, with the support 114 resting against the skin surface 20, and the slot aperture 111 ca. 1 mm from the skin surface 20. The user then applies finger pressure to the manifold 110 to move cylinder 17 slidingly over the piston 16 in the direction of the arrow, being parallel to the axis of cylinders 11 and 17, toward the reservoir 11, against the bias of spring 19. This movement forces the substance through valve 113, into manifold 110 and out through slot 111, and also moves the slot aperture 111 across the skin surface 20 in the cylindrical axis direction and transverse to the length direction of the slot 110. It is seen from FIGS. 1 to 5 that the nozzle 111 is shaped and aligned to direct flow of the substance in a direction indicated by arrows in FIG. 5 perpendicular to the direction in which the nozzle 111 is moved adjacent to the skin surface 20 and perpendicular to the length direction of the slot shaped aperture of the nozzle 111. This causes the substance to be deposited as a film of substantially uniform thickness 21 on the surface 20. The limit of this movement is defined by the abutment of the piston 16 against the end of cylinder 17 adjacent to manifold 110 (or alternatively by the abutment of manifold 110 against the end of cylinder 18), resulting in a metered dose of the substance being deposited in an area having a length defined by this limited movement. The amplitude of the reciprocal movement of cylinder 17 is ca. 3-4 cm.

The dispensing container is now in the configuration shown in FIGS. 3 and 4, showing a sectional plan view in FIG. 3 corresponding to FIG. 1, and a sectional side view in FIG. 4 corresponding to FIG. 2. Spring 19 is compressed. When the user's finger pressure is released at the end of this outlet stroke the spring 19 returns the cylinder to the position shown in FIGS. 1 and 2. This causes further substance 12 to be drawn into the pump cylinder from container 11 via the inlet 15, the valve 113 preventing suck-back of substance from the manifold 110. At the same time the floating piston 14 moves along the cylindrical container from left to right as shown to make up the volume of substance 12 dispensed from the container 11.

FIG. 6 shows a perspective view of the dispensing container of FIGS. 1 to 4, showing the disposition of the legs 114.

It is seen that a constructed line between the parts of the legs 114 and nozzle 111 which in use are closest to or in contact with the skin is substantially parallel to the direction along which the cylinder 17 of the pump reciprocates. As seen in FIG. 4 the extremities of legs 114 furthest from container 11, and the slot shaped aperture of nozzle 111 are in a plane substantially parallel to this direction.

FIG. 7 shows an alternative construction of the dispensing container 10, parts analogous to the dispensing containers of FIGS. 1-6 being numbered analogously. The dispensing container 10 has a container 11 with an outer profile 115 shaped and positioned relative to the nozzle 111 such that when in use this outer profile 115 is placed against a surface such as the user's skin, analogously to the support legs 114 the nozzle is positioned at a suitable distance from or in contact with the surface. The profile 115 is substantially planar in a direction substantially parallel to the direction along which the pump 15-19 reciprocates, and the slot shaped outlet aperture of nozzle 111 is in the plane of this planar surface 115.

The dispensing container 10 may include other features not shown. For example the nozzle 111 may be provided with a removable cover to prevent contamination or loss of residual substance left within the manifold 111 after dispensing of the substance. For example the cylinder 17 or 18, or piston 16 may be provided with relatively moveable end-stops so that the movement of the manifold 110 in the cylindrical axis direction may be set to a variable pre-determined limit to control the volume of substance dispensed and/or the length over which it is dispensed. The cylinder 17 and piston 16 may be provided with twist-lock means to prevent operation of the pump 16,17 until the twist-lock means have been disengaged.

The invention claimed is:

1. A dispensing container for application of a fluid film forming substance to a surface being a user's skin, comprising;
   a reservoir, elongated along a long axis direction and having longitudinally opposed ends, and adapted to contain the fluid film forming substance,
   a dispensing nozzle adapted to apply the film forming substance to the surface,
   a means to send the substance from the reservoir through the dispensing nozzle, said means comprising a hand-operable reciprocating pump located between the container and the dispensing nozzle, the pump having an inlet communicating with the reservoir and an outlet communicating with the nozzle, said pump comprising pump parts which are relatively reciprocally moveable in a reciprocation direction parallel to the long axis direction, such that a relative movement of the parts in a first direction draws substance from the reservoir into the pump and a reciprocal relative movement of the pump parts in the opposite second direction sends the substance through the dispensing nozzle to be applied onto the surface,
   the dispensing nozzle being connected to one of said relatively reciprocally pump parts such that the dispensing nozzle moves in the reciprocation direction as the pump parts move reciprocally, and wherein;
   the dispensing nozzle comprises an elongate slot shaped aperture through which the substance flows onto the surface, and the elongate direction of the slot-shaped aperture is transverse to the direction of reciprocal motion of the pump parts,
   and wherein the container is provided with a support by which the dispensing container may be held against the surface skin whilst the nozzle moves during the reciprocal movement of the pump parts, said support comprising either;
   one or more leg extending externally from the container in a direction transverse to the long axis direction, each leg ending in an extremity such that the length direction of the slot-shaped aperture and the extremity or extremities lie in a plane parallel to the long axis direction;
   or said support comprising an outer profiled surface of the container which is planar in a direction parallel to the long axis direction, and the length direction of the slot-shaped aperture is coplanar with said outer profiled surface.

2. A dispensing container according to claim 1 the slot shaped aperture of the dispensing nozzle has a width across its elongate length direction of 0.1-1 mm, and a length along its longitudinal direction of 1-2 cm.

3. A dispensing container according to claim 1 wherein the dispensing nozzle is shaped and aligned to direct flow of the substance in a direction transverse to the reciprocation direction and transverse to the elongate length direction of the slot shaped aperture.

4. A dispensing container according to claim 1 wherein the dispensing nozzle comprises a manifold into which substance is sent from the reservoir and the slot shaped aperture comprises an outlet opening of the manifold and the manifold is constructed so that a uniform outlet flow of substance is achieved along the whole length of the slot shaped aperture.

5. A dispensing container according to claim 4 wherein the manifold is a centre-fed coat hanger manifold.

6. A dispensing container according to claim 4 wherein the manifold comprises a cavity which, as cut in a direction perpendicular to the reciprocation direction is of an overall generally triangular shape with the slot shaped aperture along a lower base edge of the cavity and having an inlet opening into the manifold in the upper half of the triangular shape.

7. A dispensing container according to claim 1 wherein the pump parts are biased toward movement in the second direction, with a one way valve between the pump and the nozzle biased toward flow of substance from the pump toward the nozzle, the nozzle comprising a manifold into which the substance is pumped from the reservoir and having the slot shaped aperture therein.

* * * * *